(12) United States Patent
Kakinuma et al.

(10) Patent No.: US 11,873,514 B2
(45) Date of Patent: Jan. 16, 2024

(54) METHOD OF SCREENING FOR A SUBSTANCE THAT ACTS ON A CELL MASS

(71) Applicant: LSI MEDIENCE CORPORATION, Tokyo (JP)

(72) Inventors: Hideaki Kakinuma, Tokyo (JP); Yukiko Shimada, Tokyo (JP); Hiroaki Inoue, Tokyo (JP); Takashi Morikawa, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 0 days.

(21) Appl. No.: 18/146,108

(22) Filed: Dec. 23, 2022

(65) Prior Publication Data

US 2023/0131630 A1 Apr. 27, 2023

Related U.S. Application Data

(62) Division of application No. 16/494,273, filed as application No. PCT/JP2018/010247 on Mar. 15, 2018, now Pat. No. 11,549,100.

(30) Foreign Application Priority Data

Mar. 16, 2017 (JP) .................. 2017-051612

(51) Int. Cl.
*C12N 5/09* (2010.01)
*G01N 33/50* (2006.01)

(52) U.S. Cl.
CPC ....... *C12N 5/0693* (2013.01); *G01N 33/5011* (2013.01); *C12N 2513/00* (2013.01); *C12N 2533/10* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

2013/0012404 A1   1/2013   Inoue
2014/0221225 A1   8/2014   Danen et al.
(Continued)

FOREIGN PATENT DOCUMENTS

| CN | 106148285 A | 11/2016 |
|---|---|---|
| WO | WO 2011/077894 A1 | 6/2011 |
| WO | WO 2016/047801 A1 | 3/2016 |

OTHER PUBLICATIONS

Office Action and Search Report issued in Chinese Application No. 201880018522.0, dated Apr. 14, 2023.
(Continued)

*Primary Examiner* — David W Berke-Schlessel
(74) *Attorney, Agent, or Firm* — Knobbe, Martens, Olson & Bear, LLP

(57) ABSTRACT

A method of screening for a substance that acts on a cell mass includes producing a cell mass by three-dimensional culture of primary cancer cells using a tumor tissue, adding a test substance to the cell mass, and evaluating an action of the test substance on the cell mass. The cell mass is produced by culturing cells obtained from the tumor tissue in a medium containing a 5% v/v or less extracellular matrix on a substantially low-adhesive cell culture substrate and producing the cell mass of the primary cancer cells.

20 Claims, 14 Drawing Sheets

| PLATE USED *1 | PrimeSurface | Corning ULA Round-bottom | Corning ULA Flat-bottom | Elplasia | NanoCulture Plate | 96-WELL MICROPLATE |
|---|---|---|---|---|---|---|
| PHASE-CONTRAST MICROSCOPE IMAGE | Day 7 | Day 10 | Day 7 | Day 4 | Day 7 | Day 7 |
| | Day 14 | Day 17 | Day 14 | Day 14 | Day 14 | Day 14 |
| CELL MASS FORMATION | YES | YES | YES | YES | YES | YES |
| ADHESION OF FIBROBLASTS *2 | NO | NO | NO | NO | YES | YES |

(56) References Cited

U.S. PATENT DOCUMENTS

2015/0329829 A1 11/2015 Shen et al.
2018/0355322 A1 12/2018 Tsukamoto et al.

OTHER PUBLICATIONS

Tissue Culture Technology—Basics—(Soshiki Baiyo no Gijutsu-Kisohen-), the 3rd edition, Asakura Publishing Co., Ltd., 1996, pp. 93-96.
Low Cell Adhesion Products PrimeSurface, Sumitomo Bakelite Co, LTD; URL: https://www.sumibe.co/jp/english/products/s-bio/cell-culture/primesurface-96u/index.html (2016).
Bialecka et al., "Three-dimensional cell culture model utilization in cancer stem cell research: 3D cell culture models in CSCs research", Biological Reviews, vol. 92, No. 3, 2016. pp. 1505-1520.
Sato, T., et al., Single Lgr5 Stem Cells Build Crypt-Villus Structures in vitro Without a Mesenchymal Niche, Nature 459:262-265, 2009.
Sato, T., et al., Long-Term Expansion of Epithelial Organoids From Human Colon, Adenoma, Adenocarcinoma, and Barrett's Epithelium, Gastroenterology 141(5)1762-1772, 2011.
Gao, et al., Organoid Cultures Derived From Patients With Advanced Prostate Cancer, Cell 159(1):176-187, 2014.
Boj, S.F., et al., Organoid Models of Human and Mouse Ductal Pancreatic Cancer, Cell 160(1):324-338, 2015.
Cho et al., "An Integrative Approach to Precision Cancer Medicine Using Patient-Derived Xenografts", Molecules and Cells, 39(2): 77-85, 2016.
Saunders, J.H., et al., Individual Patient Oesophageal Cancer 3D Models for Tailored Treatment, Oncotarget, Advance Publications 2016, 14 pages.
Kessel et al., "High-Throughput 3D Tumor Spheroid Screening Method for Cancer Drug Discovery Using Celigo Image Cytometry", SLAS Technology, 22(4): 454-465, 2017.
Kondo, J., et al., Retaining Cell-Cell Contact Enables Preparation and Culture of Spheroids Composed of Pure Primary Cancer Cells From Colorectal Cancer, Proceedings of the National Academy of Sciences 108(15):6235-6240, Apr. 12, 2011.
Sakamoto, R., et al., Time-Lapse Imaging Assay Using the BioStation CT: A Sensitive Drug-Screening Method for Three-Dimensional Cell Culture, Cancer Science 106(6):757-765, 2015.
Ivascu, A., and M. Kubbies, Rapid Generation of Single-Tumor Spheroids for High-Throughput Cell Function and Toxicity Analysis, Journal of Biomolecular Screening 11(8):922-932, 2006.
Pisanu et al., "Lung Cancer Stem Cell Lose Their Stemness Default State after Exposure to Microgravity", BioMed Research International, vol. 2014, Article ID 470253, 8 pages (2014).
Vinci, M., et al., Advances in Establishment and Analysis of Three-Dimensional Tumor Spheroid-Based Functional Assays for Target Validation and Drug Evaluation, BMC Biology 10, Article No. 29, 2012, 20 pages.
Wang et al., "Enrichment of prostate cancer stem cells from primary prostate cancer cultures of biopsy samples", International Journal of Clinical and Experimental Pathology, 7(1): 184-193, 2014.
Extended European search report dated Nov. 20, 2020 issued in corresponding European Application No. 18767585.5.
International Search Report received in International Patent Application No. PCT/JP2018/010247 dated Jun. 5, 2018.
International Preliminary Report on Patentability received in PCT/JP2018/010247 dated Sep. 26, 2019.
Office Action issued in EP Application No. 18767585.5, dated Oct. 25, 2021.
Cho et al., "An Integrative Approach to Precision Cancer Medicine Using Patient-Derived Xenografts", Molecules and Cells, 39(2): 77-86, 2016.
Chua et al., "Single luminal epithelial progenitors can generate prostate organoids in culture", Nat. Cell Biol., 2014, 16(10), in 26 pages.
Guo et al., "Slug and Sox9 Cooperatively Determine the Mammary Stem Cell State", Cell., 2012, 148(5), in 22 pages.
Third Party Observation for EP Application No. 18767585.5, dated Nov. 13, 2023.

| PLATE USED *1 | PrimeSurface | Corning ULA Round-bottom | Corning ULA Flat-bottom | Elplasia | NanoCulture Plate | 96-WELL MICROPLATE |
|---|---|---|---|---|---|---|
| PHASE-CONTRAST MICROSCOPE IMAGE | Day 7 | Day 10 | Day 7 | Day 4 | Day 7 | Day 7 |
| | Day 14 | Day 17 | Day 14 | Day 14 | Day 14 | Day 14 |
| CELL MASS FORMATION | YES | YES | YES | YES | YES | YES |
| ADHESION OF FIBROBLASTS *2 | NO | NO | NO | NO | YES | YES |

Fig. 1

| MEDIUM CONDITION *1 | CONCENTRATION OF CORNING MATRIGEL GFR IN STEMPRO HESC SFM MEDIUM (% V/V) | | | | | | | |
|---|---|---|---|---|---|---|---|---|
| | 0 | 0.5 | 1 | 2 | 5 | 10 | 20 | 30 |
| PHASE-CONTRAST MICROSCOPE IMAGE Day 7 | | | | | | | | |
| Day 14 | | | | | | | | |
| CELL MASS FORMATION | NO | YES | YES | YES | YES | YES | YES | YES |
| HALF MEDIUM EXCHANGE *2 | Possible | Possible | Possible | Possible | Impossible | Impossible | Impossible | Impossible |

Fig. 2

| MEDIUM CONDITION *1 | CONCENTRATION OF CORNING MATRIGEL IN STEMPRO HESC SFM MEDIUM (% V/V) | | | | | | | |
|---|---|---|---|---|---|---|---|---|
| | 0 | 0.5 | 1 | 2 | 5 | 10 | 20 |
| PHASE-CONTRAST MICROSCOPE IMAGE Day 7 | | | | | | | | |
| Day 14 | | | | | | | | |
| CELL MASS FORMATION | NO | YES | YES | YES | YES | YES | YES |
| HALF MEDIUM EXCHANGE *2 | Possible | Possible | Possible | Possible | Possible | Impossible | Impossible |

Fig. 3-1

| MEDIUM CONDITION *1 | CONCENTRATION OF CULTREX BME IN STEMPRO HESC SFM MEDIUM (% V/V) | | | | | | |
|---|---|---|---|---|---|---|---|
| | 0 | 0.5 | 1 | 2 | 5 | 10 | 20 |
| PHASE-CONTRAST MICROSCOPE IMAGE Day 7 | | | | | | | |
| Day 14 | | | | | | | |
| CELL MASS FORMATION | NO | YES | YES | YES | YES | YES | YES |
| HALF MEDIUM EXCHANGE *2 | Possible | Possible | Possible | Possible | Possible | Impossible | Impossible |

Fig. 3-2

| MEDIUM CONDITION *1 | CONCENTRATION OF CELLMATRIX TYPE I-A IN STEMPRO HESC SFM MEDIUM (% V/V) | | | | | | |
|---|---|---|---|---|---|---|---|
| | 0 | 0.5 | 1 | 2 | 5 | 10 | 20 |
| PHASE-CONTRAST MICROSCOPE IMAGE | | | | | | | |
| Day 7 | | | | | | | |
| Day 14*2 | | | | | | | |
| CELL MASS FORMATION | NO | YES | YES | YES | YES | YES | YES |
| HALF MEDIUM EXCHANGE *3 | Possible | Possible | Possible | Possible | Possible | Impossible | Impossible |

Fig. 3-4

| MINIMAL ESSENTIAL MEDIUM USED *1 | StemPro hESC SFM | StemFit AK02N |
|---|---|---|
| PHASE-CONTRAST MICROSCOPE IMAGE | Day 7  Day 14  | Day 7  Day 14  |
| CELL MASS FORMATION | YES | YES |

| CANCER SPECIES OF PDX TUMOR *1 | PANCREATIC CANCER 1 | PANCREATIC CANCER 2 | LUNG SQUAMOUS CELL CARCINOMA 1 | LUNG SQUAMOUS CELL CARCINOMA 2 | LUNG SQUAMOUS CELL CARCINOMA 3 | GASTRIC CANCER 1 | LARGE BOWEL CANCER 1 |
|---|---|---|---|---|---|---|---|
| PHASE-CONTRAST MICROSCOPE IMAGE | Day 14 | Day 14 | Day 14 | Day 14 | Day 17 | Day 14 | Day 14 |
|  | Day 21 | Day 21 | Day 21 | Day 21 | Day 24 | Day 21 | Day 21 |
| CELL MASS FORMATION | YES | YES | YES | YES | YES | YES | YES |

Fig. 5

METHOD OF SCREENING FOR A SUBSTANCE THAT ACTS ON A CELL MASS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to a method of producing a cell mass by three-dimensional culture of primary cancer cells using a tumor tissue, and a cell mass, a screening method, a determination method, and a kit.

BACKGROUND

Established cancer cells (cancer cell lines) have been conventionally used for a method of evaluating tumor ex vivo. However, it has been pointed out that cancer cell lines have lost the nature of their original tumor due to the homogenization of population and the accumulation of gene mutations as a result of adaptation to an ex vivo environment with long time cell culture. In addition, it has been also pointed out that the limited number of cancer cell lines cannot fully explain the pathological conditions of tumor composed of cancer cells with diverse genetic heterogeneity. Therefore, in order to understand a tumor more correctly, a culture system using primary cells of the tumor has been gaining attention. In addition to a tumor obtained from a patient, a xenograft (patient-derived xenograft, PDX) tumor produced by grafting the tumor to an immunodeficient animal is used.

Basic steps of culturing primary cells of a tumor include physically or enzymatically dispersing an extracted tumor and seeding the obtained dispersed cells with a medium in a culture container, thereby allowing the cells to proliferate in a $CO_2$ incubator (Non Patent Literature 1: Tissue Culture Technology—Basics— (*Soshiki Baiyo no Gijutsu—Kisohen—*), the 3rd edition, Asakura Publishing Co., Ltd., 1996). In order to improve proliferation of cancer cells or inhibit excessive proliferation of non-cancer cells (especially fibroblasts), cell separation by density gradient centrifugation, coating of a culture container with an extracellular matrix, use of a serum-free medium, cell separation based on differences in sensitivity to trypsin enzymes and antibiotics, and the like have been conducted. However, even with such creative techniques, it is difficult to achieve cancer cell proliferation with high probability, and a more reliable culture method has been desired.

In recent years, a method of three-dimensionally culturing cells has been gaining attention as a method of culturing primary cancer cells. A first example of such a method is the organoid culture method developed by Clevers et al. from the Hubrecht Institute (Non Patent Literature 2: Sato, Toshiro, et al. "Single Lgr5 stem cells build crypt villus structures in vitro without a mesenchymal niche," Nature 459.7244 (2009): 262-265; Non Patent Literature 3: Sato, Toshiro, et al. "Long-term expansion of epithelial organoids from human colon, adenoma, adenocarcinoma, and Barrett's epithelium," Gastroenterology 141.5 (2011): 1762-1772). Organoid culture is a method of forming a cell mass (organoid) by self-organization of living stem cells. Specifically, living stem cells are embedded in extracellular matrix gel and cultured in an optimal medium. By applying this technique to primary cancer cells, they have established a method of culturing large bowel cancer (Non Patent Literature 3), prostate cancer (Non Patent Literature 4: Gao, Dong, et al. "Organoid cultures derived from patients with advanced prostate cancer," Cell 159.1 (2014): 176-187), and pancreatic cancer (Non Patent Literature 5: Boj, Sylvia F., et al. "Organoid models of human and mouse ductal pancreatic cancer," Cell 160.1 (2015): 324-338). However, this method requires embedding cells in gel at low temperatures, and thus, lacks high-throughput performance, and is not sufficiently versatile in drug development and the like.

A second example thereof is the 3D-tumor growth assay (3D-TGA) method developed by Molecular Response LLC and others. This method is similar to the first method in that cells are embedded in extracellular matrix gel and cultured using an optimal medium, but is different in that preculture is performed in a culture container coated with an extracellular matrix in the prior step, and grown cancer-associated fibroblasts (CAFs) or mesenchymal stem cells (MSCs) are optionally embedded with cancer cells in extracellular matrix gel (Non Patent Literature 6: Saunders, John H., et al. "Individual patient oesophageal cancer 3D models for tailored treatment," Oncotarget (2016)). This method also requires embedding cells in gel at low temperatures as in the first method, and thus, lacks high-throughput performance.

A third example thereof is the culture method using a non-uniformly dispersed cell mass having a diameter of from 40 to 100 μm (cancer tissue-originated spheroid, CTOS) developed by Inoue et al. from the Center for Adult Diseases (the CTOS method)(Non Patent Literature 7: Kondo, Jumpei, et al. "Retaining cell-cell contact enables preparation and culture of spheroids composed of pure primary cancer cells from colorectal cancer" Proceedings of the National Academy of Sciences 108.15 (2011): 6235-6240). Specifically, the obtained CTOSs are seeded on a non-adhesive plate and culture is conducted while suspending the CTOSs using an optimal medium. As cancer cells of CTOSs can proliferate without being embedded in extracellular matrix gel, this method does not require a temperature control operation as compared with the first and second methods. However, as the drug sensitivity test requires a complicated step of selecting and arranging CTOSs of a uniform size, high-throughput performance is poor and cancer cells have poor proliferative ability in the method as compared to the method in which cells are embedded in an extracellular matrix. Therefore, the method is insufficient in terms of practical use.

A fourth example thereof is the culture method using a cell culture plate treated for inhibiting adhesion to uniformly dispersed cancer cells developed by Nakatsura et al. from the National Cancer Center (Patent Literature 1: WO2016/047801). Specifically, it is a method in which uniformly dispersed cancer cells are seeded with a medium containing serum at 1% by volume or more on a NanoCulture Plate, which is a three-dimensional culture plate manufactured by ORGANOGENIX, Inc. so as to culture a cell mass. A culture kit (Cancer Organoid Culture Kit) is commercially available from ORGANOGENIX, Inc. As cancer cells can proliferate without being embedded in extracellular matrix gel, this method does not require a temperature control operation as compared with the first and second methods. In addition, since uniformly dispersed cancer cells are used, it is possible to uniformly seed cells without the need for special operations, the method is superior to the third method in terms of high-throughput performance. However, there are only reports using a human lung cancer tumor and a xenograft tumor of breast cancer (Non Patent Literature 8: Sakamoto, Ruriko, et al. "Time-lapse imaging assay using the BioStation CT: A sensitive drug-screening method for three-dimensional cell culture," Cancer science 106.6 (2015): 757-765). In particular, in the xenograft tumor of breast cancer, proliferation of cell mass could not be clearly confirmed, verification of versatility has remained unsatisfactory, and there is a question about practical use.

As described above, in culture of primary cancer cells using a tumor tissue, the certainty of culture performance is increasing because of the use of the three-dimensional culture methods. However, each method is problematic in terms of proliferative ability, handleability, high-throughput performance, versatility, etc. of cancer cells.

CITATION LIST

Patent Literature

Patent Literature 1: WO2016/047801

Non Patent Literature

Non Patent Literature 1: Tissue Culture Technology—Basics— (*Soshiki Baiyo no Gijutsu—Kisohen*—), the 3rd edition, Asakura Publishing Co., Ltd., 1996
Non Patent Literature 2: Sato, Toshiro, et al. "Single Lgr5 stem cells build crypt villus structures in vitro without a mesenchymal niche." Nature 459.7244 (2009): 262-265
Non Patent Literature 3: Sato, Toshiro, et al. "Long-term expansion of epithelial organoids from human colon, adenoma, adenocarcinoma, and Barrett's epithelium." Gastroenterology 141.5 (2011): 1762-1772
Non Patent Literature 4: Gao, Dong, et al. "Organoid cultures derived from patients with advanced prostate cancer." Cell 159.1 (2014): 176-187
Non Patent Literature 5: Boj, Sylvia F., et al. "Organoid models of human and mouse ductal pancreatic cancer." Cell 160.1 (2015): 324-338
Non Patent Literature 6: Saunders, John H., et al. "Individual patient oesophageal cancer 3D models for tailored treatment." Oncotarget (2016)
Non Patent Literature 7: Kondo, Jumpei, et al. "Retaining cell-cell contact enables preparation and culture of spheroids composed of pure primary cancer cells from colorectal cancer." Proceedings of the National Academy of Sciences 108.15 (2011): 6235-6240
Non Patent Literature 8: Sakamoto, Ruriko, et al. "Time-lapse imaging assay using the BioStation CT: A sensitive drug-screening method for three-dimensional cell culture." Cancer science 106.6 (2015): 757-765

SUMMARY

The invention has been made in view of the above problems. An object of the invention made by the present inventors is to provide a method of producing a cell mass by three-dimensional culture of primary cancer cells having proliferative ability and properties of handleability, versatility, and high-throughput performance, in which a tumor tissue is used as a starting material, proliferation of cells such as fibroblasts other than cancer cells is inhibited, and the cell mass includes primary cancer cells as a main component.

In order to solve the above problems, the inventors made intensive studies. As a result, they found that it is possible to produce a cell mass of primary cancer cells having high proliferative ability and properties of handleability, versatility, and high-throughput performance of cancer cells that can be used in various tests, by a three-dimensional culture method by culturing uniformly dispersed cells in suspension using a patient-derived xenograft (hereinafter also abbreviated as "PDX" in some cases) tumor as a starting material by combining an optimal culture substrate and an optimal three-dimensional culture medium. This has led to the completion of the invention.

The invention is exemplified as follows.

[1] A method of producing a cell mass by three-dimensional culture of primary cancer cells using a tumor tissue, comprising:
a three-dimensional culture step of culturing cells obtained from the tumor tissue in a medium containing a 5% v/v or less extracellular matrix on a substantially low-adhesive cell culture substrate.

[2] The method according to [1], wherein the tumor tissue is a xenograft tumor.

[3] A cell mass of primary cancer cells obtained from a tumor tissue, which is produced by the method of producing a cell mass according to [1] or [2].

[4] A method of screening for a substance that acts on a cell mass, comprising:
producing a cell mass of primary cancer cells by the method of producing a cell mass according to [1] or [2];
adding a test substance to the cell mass; and
evaluating an action of the test substance on the cell mass.

[5] A method of determining effects of a substance on a cell mass, comprising:
producing cell mass of primary cancer cells by the method of producing cell mass according to [1] or [2];
adding a test substance to the cell mass; and
evaluating effects of the test substance on the cell mass.

[6] A kit of producing a cell mass by three-dimensional culture of primary cancer cells using a tumor tissue, including:
a substantially low-adhesive cell culture substrate; and
a medium containing a 5% v/v or less extracellular matrix for a three-dimensional culture step.

Advantageous Effects of Invention

The invention has made it possible to provide a method of producing a cell mass by three-dimensional culture of primary cancer cells having proliferative ability and properties of handleability, versatility, and high-throughput performance, in which a tumor tissue is used as a starting material, proliferation of cells such as fibroblasts other than cancer cells is inhibited, and the cell mass includes primary cancer cells as a main component.

BRIEF DESCRIPTION OF THE DRAWINGS

FIG. 1 shows the results of culture in Example 2 (image): *1: a PDX tumor of pancreatic cancer (1) was used; a culture medium prepared by adding Corning Matrigel GFR to StemPro hESC SFM to yield a final concentration of 2% v/v was used; *2: in a case in which spindle-shaped cells were observed on the bottom of the plate, it was determined that there was adhesion of fibroblasts.

FIG. 2 shows the results of culture in Example 3 (image): *1: a PDX tumor of pancreatic cancer (1) was used; Prime-Surface was used; *2: it was identified as "impossible" in a case where cells or cell mass was also suctioned upon suctioning half of the medium in a well by pipetting.

FIG. 3-1 shows the results of culture (Corning Matrigel) in Example 4 (image): *1: a PDX tumor of pancreatic cancer (1) was used; PrimeSurface was used; *2: it was identified as "impossible" in a case where cells or cell mass was also suctioned upon suctioning half of the medium in a well by pipetting.

FIG. 3-2 shows the results of culture (Cultrex BME) in Example 4 (image): *1: a PDX tumor of pancreatic cancer (1) was used; PrimeSurface was used; *2: it was identified as "impossible" in a case where cells or cell mass was also suctioned upon suctioning half of the medium in a well by pipetting.

FIG. 3-3 shows the results of culture (Cultrex RGF BME) in Example 4 (image): *1: a PDX tumor of pancreatic cancer (1) was used; PrimeSurface was used; *2: it was identified as "impossible" in a case where cells or cell mass was also suctioned upon suctioning half of the medium in a well by pipetting.

FIG. 3-4 shows the results of culture (Cellmatrix Type I-A) in Example 4 (image): *1: a PDX tumor of pancreatic cancer (1) was used; PrimeSurface was used; *2: 2% v/v wells were visually observed on Day 14 because focusing was not achieved in microscopy; *3: it was identified as "impossible" in a case where cells or cell mass was also suctioned upon suctioning half of the medium in a well by pipetting.

FIG. 4 shows the results of culture in Example 5 (image): *1: a PDX tumor of pancreatic cancer (1) was used; a culture medium prepared by adding Corning Matrigel GFR to minimal essential medium to yield a final concentration of 2% v/v was used; PrimeSurface was used as a culture plate.

FIG. 5 shows the results of culture in Example 6 (image): *1: a culture medium prepared by adding Corning Matrigel GFR to StemPro hESC SFM to yield a final concentration of 2% v/v was used; PrimeSurface was used as a culture plate;

FIG. 10-1 shows the results of culture in Example 11 (image).

FIG. 10-2 shows the results of culture in Example 11 (image).

DETAILED DESCRIPTION OF THE PREFERRED EMBODIMENT

Figure 3:
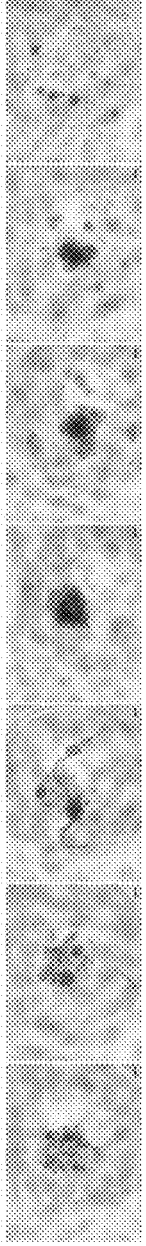

The method of producing a cell mass by three-dimensional culture of primary cancer cells using a tumor tissue of the invention is characterized by a three-dimensional culture step of culturing primary cancer cells obtained from the tumor tissue in a medium containing a 5% v/v or less extracellular matrix on a substantially low-adhesive cell culture substrate.

In general, it was considered that when primary cancer cells are subjected to three-dimensional culture in suspension, it is difficult to form a cell mass unless a special technique is used. In addition, it was considered that when using a medium containing an extracellular matrix, culture in a gel-like medium in a fixed state results in a cell mass having high proliferative ability. However, as mentioned in Examples described later, by culturing primary cancer cells in suspension in a medium containing a sol of an extracellular matrix on a substantially low-adhesive cell culture substrate, it has become possible to carry out three-dimensional culture while inhibiting proliferation of cells such as fibroblasts other than cancer cells, thereby allowing the primary cancer cells to have high proliferative ability. This has provided unexpected effects.

Accordingly, it is possible to produce a cell mass by three-dimensional culture of primary cancer cells using a tumor tissue. The cell mass has properties of handleability, versatility, and high-throughput performance of cancer cells because cells are cultured in suspension while maintaining high proliferative ability suited for various tests. The suspended state means a state in which cells can be easily moved by an operation such as pipetting, but are not adhering to a cell culture substrate or embedded in a gel-type culture solution. The size of cell mass produced by the method of the invention is not particularly limited. However, for example, the average diameter is 100 μm or more, preferably from 100 μm to 300 μm.

Hereinafter, one aspect of the method of producing a cell mass by three-dimensional culture of primary cancer cells using a tumor tissue based on a culture method according to the invention will be described.

One example of a substantially low-adhesive cell culture substrate that can be used in the invention is a low-adhesive culture substrate that enables three-dimensional suspension culture of cells. Such a substantially low-adhesive cell culture substrate may be a cell culture substrate which is made entirely low-adhesive so as to be used in three-dimensional culture, and can be, for example, a culture substrate having a hydrophilic surface or a cell culture substrate having a surface treated with a hydrophilic compound. Specific examples thereof include, for example, PrimeSurface (Sumitomo Bakelite Co., Ltd.), Corning ULA Round-bottom (Corning Incorporated), Corning ULA Flat-bottom (Corning Incorporated), and Elplasia (Kuraray Co., Ltd.). In addition, it is also possible to form a low-adhesive culture substrate by treating an adhesive cell culture substrate such that adhesiveness is inhibited. As the treatment for inhibiting adhesiveness, known treatment such as hydrophilization treatment or hydrophobization treatment can be used. In addition, it is possible to determine whether a culture substrate is low-adhesive by performing three-dimensional culture of primary cancer cells using a tumor tissue and confirming that cells such as fibroblasts other than cancer cells do not extend and proliferate in areas other than a cell mass on the substrate. In addition, the shape, processing, material, etc. of the substrate are not limited as long as it is a substantially low-adhesive cell culture substrate.

The tumor tissue that can be used in the invention may be a tissue fragment containing known cancer cells. For example, cancer cells of lymphoma, myeloma, brain tumor, breast cancer, endometrial cancer, cervical cancer, ovarian cancer, esophageal cancer, gastric cancer, appendix cancer, large bowel cancer, hepatocellular carcinoma, gallbladder cancer, cholangiocarcinoma, pancreatic cancer, adrenal cancer, gastrointestinal stromal tumor, mesothelioma, laryngeal cancer, oral cavity cancer, gingival cancer, tongue cancer, buccal mucosa cancer, salivary adenocarcinoma, carcinoma of the paranasal sinuses, maxillary cancer, carcinoma of the frontal sinus, ethmoid cancer, carcinoma of the sphenoidal sinus, thyroid cancer, renal cancer, lung cancer, osteosarcoma, prostate cancer, testicular tumor, renal cell carcinoma, bladder cancer, rhabdomyosarcoma, skin cancer, anal cancer, and other various cancers, various stem cells, various progenitor cells, mesenchymal progenitor cells, ES cells, and iPS cells can be mentioned. Cells are not limited to a single type of cells, but may be a population of cells of different types. The origin of a tumor tissue is not particularly limited. Examples thereof include animals belonging to primates including humans and monkeys, animals belonging to rodents such as mice and rats, animals belonging to the order Lagomorpha, animals belonging to the order Carnivora such as dogs and cats, animals belonging to the order Artiodactyla such as pigs, and animals belonging to the order Perissodactyla such as bovines and horses. In addition to a tumor tissue obtained from a patient, a xenograft (patient-derived xenograft, PDX) tumor produced by grafting the tumor tissue to an immunodeficient animal can also be used. The patient-derived xenograft tumor can be prepared by making use of a known method (Non Patent Literature 9: Cho, Sung-Yup, et al. "An integrative approach to precision cancer medicine using patient-derived xenografts," Molecules and cells 39.2 (2016): 77).

According to the invention, even with the use of a PDX tumor, it is possible to produce a cell mass by three-dimensional culture of primary cancer cells having high proliferative ability and properties of handleability, versatility, and high-throughput performance which can be used in various tests. It is therefore particularly preferable that a PDX tumor is a tumor of interest. PDX tumors enable the development of anticancer drugs with high clinical predictability using patient-derived tumors, and can be used also for determination of therapeutic effects. It is therefore particularly preferable that a PDX tumor can be a tumor of interest.

In addition, it is possible to use, as a tumor tissue that can be used in the invention, either a fresh tumor prepared by surgically extracting a tumor and immersing it in a tissue preservation solution (such as physiological saline or HBSS) or a cryopreserved tumor prepared by immersing a fresh tumor in a cryopreservation solution (such as CELL-BANKER 1) and cryopreserving it while keeping cells alive. A person skilled in the art can select a preservation method from known methods as appropriate and use the method.

A known method can be used as a three-dimensional culture method that can be used in the invention unless otherwise specified.

A known method can be adopted as a step of preparing primary cancer cells in a method of producing a cell mass by three-dimensional culture of primary cancer cells using a tumor tissue that can be used in the invention. For example, a method in which cells are collected from a tissue fragment containing cancer cells or a method in which the tissue fragment is directly used can be mentioned. However, in consideration of handleability, test repeatability, and the like, the method in which cells are collected is preferable.

In the method in which cells are collected from a tissue fragment containing cancer cells, for example, a tumor tissue fragment extracted from the living body is treated by enzyme treatment, density gradient centrifugation treatment, filter treatment, treatment using magnetic beads or a flow cytometer, or the like as necessary for separation and purification. Enzyme treatment is preferable because the treatment method is convenient such that cancer cells dispersed as single cells can be easily obtained. The resulting cell group may be a population of cells in different stages of differentiation originating from the same tissue.

The three-dimensional culture method that can be used in the invention includes culturing primary cancer cells obtained from a tumor tissue in a medium containing a 5% v/v or less extracellular matrix on the above-described substantially low-adhesive cell culture substrate. The extracellular matrix, the medium, and the primary cancer cells may be mixed in any order thereof. For example, a medium containing the 5% v/v or less extracellular matrix in a sol state is prepared and mixed with the primary cancer cells, and the mixture is seeded on the substantially low-adhesive culture plate. In the case of using the 5% v/v or less extracellular matrix, the primary cancer cells can be cultured in suspension.

Since the cells can be cultured in suspension, handleability of the cells is easy, the cells can be readily used in various tests, and a mechanical operation of the cells becomes possible. Thus, the cells can be readily used in high-throughput tests, which is preferable.

One example of an extracellular matrix that can be used in the invention includes an extracellular matrix that can be used in a known three-dimensional culture method. Examples thereof include, for example, collagen I, collagen IV, fibronectin, laminin, vitronectin, entactin, gelatin, elastin, proteoglycan, glucosaminoglycan, chondroitin sulfate, dermatan sulfate, heparan sulfate, heparin, keratan sulfate, Matrigel (trademark: Corning Incorporated), Matrigel GFR (trademark: Corning Incorporated), Cultrex BME (trademark: Trevigen, Inc.), Cultrex RGF BME (trademark: Trevigen, Inc.), and Cellmatrix Type I-A (trademark: Nitta Gelatin Inc.).

The concentration of an extracellular matrix that can be used in the invention can be set such that primary cancer cells obtained from a tumor tissue can be three-dimensionally cultured in suspension. It may be 5% v/v or less and 2.5% v/v or less. Although the lower limit thereof is not particularly limited, it is preferably 0.1% v/v or more, more preferably 0.2% v/v or more, and particularly preferably 0.5% v/v or more. A person skilled in the art can set the concentration as appropriated depending on the type of the primary cancer cells, etc.

The density of cells to be seeded that can be used in the invention can be set such that primary cancer cells obtained from a tumor tissue can normally live in the form of cell mass produced by a three-dimensional culture method. The primary cancer cells can be seeded at a cell density of usually from $3 \times 10^3$ to $7 \times 10^4$ cells/cm$^2$. However, it is possible to set a preferable cell density as appropriate depending on culture conditions or culture instruments to be used. In addition, known conditions can be used as culture conditions. For example, the culture temperature is preferably from 20° C. to 45° C., more preferably from 30° C. to 42° C., and particularly preferably from 35° C. to 39° C., and the pH of a culture solution is preferably pH 7 to 8. In addition, the culture period can be set as appropriate depending on a test method of interest. However, it is preferably from 2 days to 30 days and more preferably from 7 days to 14 days. The cell density can be stably maintained at high levels even in a particularly long period of time (about 10 days or more), resulting in a high value of use.

As a medium that can be used in the invention, a cell culture base medium, a differentiation medium, a medium specialized for primary culture, or the like can be optionally used. Examples thereof include, for example, Dulbecco's Modified Eagle Medium (DMEM), Glasgow's MEM (GMEM), RPMI1640, Ham's F12 medium, and serum-free medium (such as MCDB medium). Further, a medium prepared by adding serum, various growth factors (insulin, transferrin, selenium salt, and dexamethasone), and a differentiation inducer to any of these media can be used.

A cell mass that can be produced by three-dimensional culture of primary cancer cells using a tumor tissue according to the invention can be used in various test methods, for example but not limited to, a method of screening for a substance that acts on the cell mass and a method of determining effects of a substance on the cell mass. The cell mass has high cell proliferation ability that can be utilized in various test methods and also has handleability, versatility, and high-throughput performance because it exists in suspension, and thus, the cell mass is advantageous in that it can be readily used in various tests.

A person skilled in the art can carry out a method of screening for a substance that acts on a cell mass according to the invention by modifying a known method as appropriate. For example, in accordance with the invention, a method of screening for a substance that acts on a cell mass includes: a step of producing a cell mass by three-dimensional culture of primary cancer cells using a tumor tissue; a step of adding a test substance to the cell mass; and a step of evaluating an action of the test substance on the cell mass. Examples of a substance that acts on a cell mass include substances capable of directly and/or indirectly acting on the cell mass such as, for example, anticancer drugs, various compounds, antibodies, antibody-drug conjugates, nucleic acids, peptides, viruses, and cells (such as NK cells, TCR-T cells, and CAR-T cells). For example, as it is possible to screening for a substance capable of inhibiting proliferation of the cell mass, the substance can be used for the development of anticancer drugs.

A person skilled in the art can carry out a method of determining effects of a substance on the cell mass of the invention by modifying a known method as appropriate. For example, in accordance with the invention, a method of determining effects of a substance on a cell mass includes: a step of producing a cell mass by three-dimensional culture of primary cancer cells using a tumor tissue; a step of adding a test substance to the cell mass; and a step of evaluating effects of the test substance on the cell mass. Examples of a test substance for determining the effects include, for example, anticancer drugs, various compounds, antibodies, antibody-drug conjugates, nucleic acids, peptides, viruses, and cells (such as NK cells, TCR-T cells, and CAR-T cells). For example, by identifying an anticancer drug capable of inhibiting proliferation of the cell mass from among various anticancer drugs and administering the anticancer drug to a patient as the origin of the cell mass, it is possible to enhance treatment effects. This can support selection of a treatment method. It is also possible to use the anticancer drug to a patient having a similar origin to the cell mass without limiting to a combination of the cell mass and the patient as the origin of the cell mass.

Known anticancer drugs can be used. Examples thereof include, for example, actinomycin D, melphalan, busulfan, carboplatin, cisplatin, cyclophosphamide, dacarbazine, oxaliplatin, procarbazine, temozolomide, ifosfamide, liposomal doxorubicin, doxorubicin, daunorubicin, epirubicin, idarubicin, mitomycin C, bleomycin, mitoxantrone, cladribine, fluorouracil, mercaptopurine, pemetrexed, methotrexate, cytarabine, nelarabine, capecitabine, fludarabine, gemcitabine, pentostatin, vincristine, eribulin, paclitaxel, vinblastine, irinotecan, docetaxel, etoposide, vinorelbine, nogitecan, paclitaxel, tretinoin, bevacizumab, trastuzumab, panitumumab, cetuximab, ibritumomab tiuxetan, rituximab, gemtuzumab ozogamicin, everolimus, erlotinib, lapatinib, gefitinib, imatinib, dasatinib, sunitinib, sorafenib, bortezomib, tamibarotene, nimustine, ranimustine, enocitabine, carmofur, cytarabine ocfosphate, tegafur, tegafur-uracil, tegafur-gimeracil-oteracil potassium, doxifluridine, hydroxycarbamide, sobuzoxane, vindesine, aclarubicin, amrubicin, zinostatin stimalamer, pirarubicin, peplomycin, and nedaplatin.

In addition, the cell mass may be directly used in the culture solution for various tests or transferred to another container for used in various tests after being cultured by the three-dimensional culture method. In a case in which the cell mass is transferred to another container, the cell mass can be collected by a known method. A person skilled in the art can select carry out the method as appropriate. In addition, the cell mass is advantageous in that it can be readily collected because it is cultured in suspension.

Examples of various test methods include known test methods such as, for example, cell proliferation tests (MTT assay, ATP assay, etc.), viable/dead cell staining analysis, phenotype screening (for example, analysis of epithelial-mesenchymal transition such as cell morphology change), histopathological analysis (HE staining, immunohistochemical staining, etc.), and biochemical analysis (gene mutation analysis, mRNA expression analysis, protein expression analysis, exosome analysis, etc.). A person skilled in the art can predetermine a test method as appropriate depending on a method of screening for the above-described substance, a method of determining effects of the substance, and the like.

According to the invention, it becomes possible to perform various test methods using an ordinary automatic dispenser in seeding of cells on a 96-well or 384-well plate, medium exchange, addition of a drug solution, addition of an assay reagent, acquisition of electronic data on the subsequent luminescence or using a fluorescence measurement device, acquisition of electronic data on image analysis using an automatic image analyzer, or the like in a convenient manner or in a high-throughput manner A person skilled in the art can readily confirm by a known method that cell mass produced by three-dimensional culture of primary cancer cells using a tumor tissue according to the invention inhibits proliferation of cells such as fibroblasts other than cancer cells and has high proliferative ability because of containing primary cancer cells as a main component so that the cell mass reflects the living body, and therefore, the cell mass can be used for various applications. For example, it is possible to confirm whether a cell mass has a function similar to a tumor in the living body by visually observing cell mass formation, evaluating proliferative ability of cells, evaluating effects of a known substance on the cell mass, or evaluating whether the cell mass can form a tumor when the cell mass obtained from an animal is regrafted to the animal.

As the kit of the invention, a kit of producing a cell mass by three-dimensional culture of primary cancer cells using a tumor tissue, which includes a substantially low-adhesive cell culture substrate and a medium containing a 5% v/v or less extracellular matrix for the three-dimensional culture step, can be mentioned. Regarding the medium containing a 5% v/v or less extracellular matrix for the three-dimensional culture step, an extracellular matrix and a medium may be separately provided so as to be mixed before use of the kit or an extracellular matrix and a medium may be mixed in advance and then provided. In addition, manufacturer's instructions, etc. contain the description of a substantially low-adhesive cell culture substrate, an extracellular matrix, and a medium that can be used in the method of producing a cell mass of the invention such that a user of the kit can obtain the kit components. In addition, for example, materials for a cell culture substrate, a medium, an extracellular matrix, and the like or a method of using the kit which can be used in the method of producing a cell mass of the invention can be mentioned.

EXAMPLES

Hereinafter, the invention will be described in more detail by way of examples.

However, the invention is not limited by these examples.

Example 1: Collection of Tumor Tissue and Cancer Cell Dispersion Treatment

A human cancer patient-derived xenograft (hereinafter referred to as "PDX") tumor, which was subcutaneously grown in an immunodeficient mouse [super SCID mouse (strain name C3H/HeJ/NOs-scid; LPS-nonresponder)], was aseptically extracted in a safety cabinet according to an ordinary method, and every necrotic area of the tumor was removed with surgical scissors. The tumor was immediately immersed in a Japanese Pharmacopoeia saline solution and preserved on ice. Next, the Japanese Pharmacopoeia saline solution was removed from the tumor, and the tumor was washed three times repeatedly with specimen treatment solution (included in a Cancer Organoid Culture Kit, ORGANOGENIX, Inc.).

Cancer cell dispersion treatment was performed as described below as a preparation step for three-dimensional culture. The washed tumor was placed in a 10-cm petri dish on ice, shredded to a size of about 1 mm square with surgical scissors, and collected in a 50-mL tube. A dispersion solution (included in a Cancer Organoid Culture Kit, ORGANOGENIX, Inc.) was added to the tube. Tumor fragments were enzymatically treated at 37° C. for 60 min while the tube was shaken in a water bath. The reaction was weakened by adding twice the amount of a specimen treatment solution to the reaction solution. The undispersed residues were removed by passing the mixture through a 100-μm cell strainer. The tube and the cell strainer were washed with an appropriate amount of the specimen treatment solution, and cells were collected and centrifuged at 300×g for 5 min. The supernatant was removed. Then, the specimen treatment solution was added to resuspend the resulting cell pellet and centrifuged at 300×g for 5 min. Thereafter, the cell pellet was resuspended with an appropriate amount of the specimen treatment solution and cell counting was performed. After confirming that the cells were separated into single cells, the cells were used in the following experiment.

Example 2: Seeding and Culture of Cells in Three-Dimensional Culture Plate

At first, it was examined whether it would be possible to perform three-dimensional culture using a PDX tumor by means of a Cancer Organoid Culture Kit (ORGANOGENIX, Inc.) described as capable of three-dimensional culture of primary cancer cells. A Cancer Organoid Culture Kit is for a method of performing culture with a plate prepared by allowing a low-adhesive plate to have an uneven scaffolding structure for forming a cell mass of cancer cells and a medium containing serum at 1% by volume or more.

Primary cancer cells were prepared using PDX tumor of pancreatic cancer (1) (procured from National Institutes of Biomedical Innovation, Health and Nutrition) in accordance with Example 1. The necessary amount of cells counted after dispersion treatment were collected in a 15-mL tube, and the supernatant was removed by centrifugation at 300×g for 5 min. Thereafter, a cell suspension was prepared using NanoCulture Medium P type (included in a Cancer Organoid Culture Kit, ORGANOGENIX, Inc.) so that the cell count was $1 \times 10^5$ cells/mL. NanoCulture Medium P type in an amount of 150 μL was added to NanoCulture Plate (included in a Cancer Organoid Culture Kit, ORGANOGENIX, Inc.) serving as a three-dimensional culture plate, followed by centrifugation at 700×g for 5 min. The plate was left to stand at 37° C. for 10 min for prewetting. The cell suspension in an amount of 100 μL was added to the plate, and static culture was initiated in a $CO_2$ incubator set to 37° C. and 5% $CO_2$. The seeded cell count was $1 \times 10^4$ cells/250 μL/well, and the day of seeding was determined to be Day 0. A half of medium exchange was performed as appropriate. As a result, no clear cell mass was formed and adhesion of spindle-shaped fibroblasts to the plate bottom was observed. It was therefore found difficult to apply a Cancer Organoid Culture Kit of ORGANOGENIX, Inc. directly to the PDX tumor of pancreatic cancer (1).

In order to achieve culture in suspension, an extracellular matrix, which is usually used in the gel form, was prepared to be contained in a medium in a sol state, and it was examined whether it would be possible for primary cancer cells to form a cell mass without expansion or proliferation of cells such as fibroblasts other than cancer cells.

As described above, the necessary amount of cells counted were collected in a 15-mL tube, and the supernatant was removed by centrifugation at 300×g for 5 min Thereafter, a cell suspension was prepared so that the cell count was $5 \times 10^4$ cells/mL using a medium prepared by adding Corning Matrigel GFR (Corning Incorporated) to StemPro hESC SFM (Thermo Fisher Scientific K.K.) to yield a final concentration of 2% v/v. The cell suspension in an amount of 200 μL was seeded in PrimeSurface (Sumitomo Bakelite Co., Ltd.), Corning ULA Round-bottom (Corning Incorporated), Corning ULA Flat-bottom (Corning Incorporated), or Elplasia (Kuraray Co., Ltd.), which is a three-dimensional culture plate as an ordinary low-adhesive plate, or a 96-well microplate (Corning Incorporated), which is an ordinary adhesive plane (two-dimensional) culture plate, and static culture was initiated in a $CO_2$ incubator set to 37° C. and 5% $CO_2$. Similarly, a cell suspension was prepared to yield $1 \times 10^5$ cells/mL in NanoCulture Plate, 100 μL of the cell suspension was added to the plate prewetted with 150 μL of a medium for seeding, and static culture was initiated in a $CO_2$ incubator set to 37° C. and 5% $CO_2$. The seeded cell count was $1 \times 10^4$ cells/200 μL/well (except NanoCulture Plate) or $1 \times 10^4$ cells/250 μL/well (NanoCulture Plate), and the day of seeding was determined to be Day 0. A half of medium exchange was performed as appropriate.

Figures 1, 10:
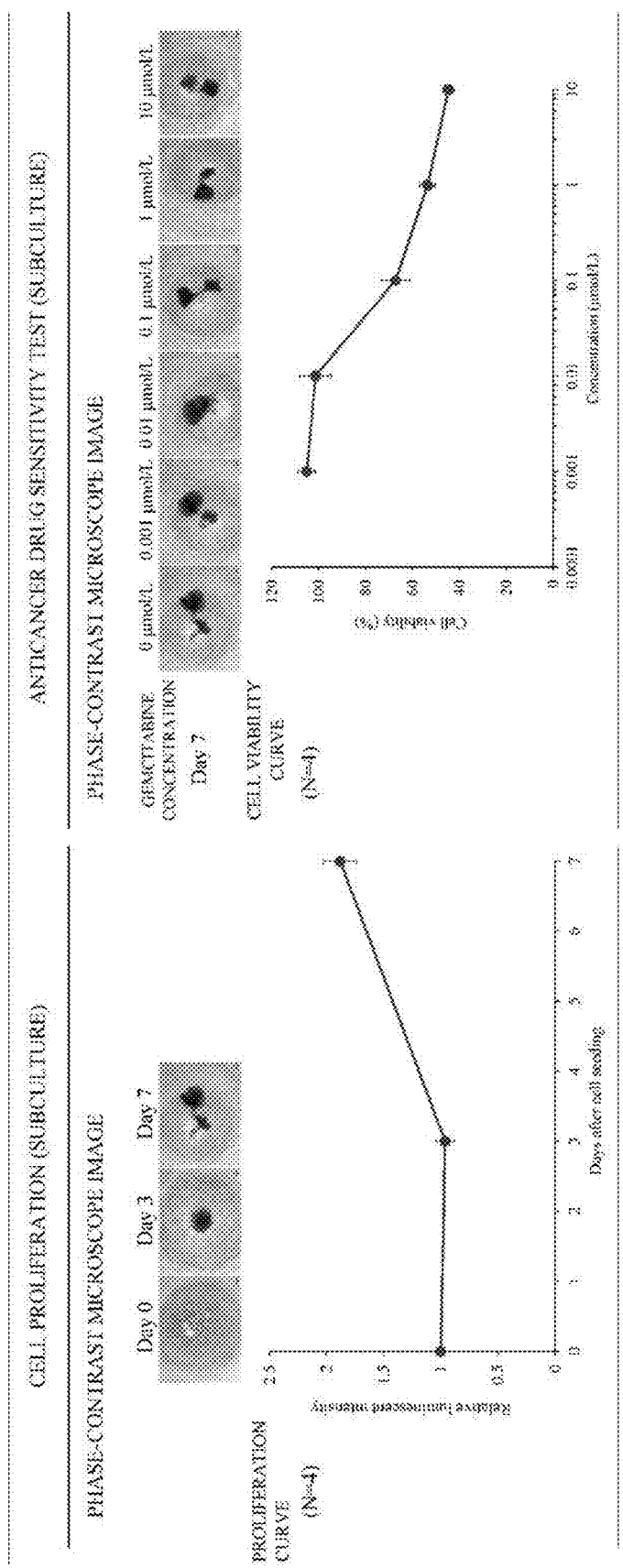

FIG. 1 shows the results. Cell morphology was confirmed by a phase-contrast microscope. It was determined whether or not a cell mass was formed based on the morphology, and in a case in which spindle-shaped cells were observed on the bottom of the plate, it was determined that there was adhesion of fibroblasts. As a result, in any of PrimeSurface, Corning ULA Round-bottom, Corning ULA Flat-bottom, or Elplasia, which is a three-dimensional culture plate as an ordinary low-adhesive plate, adhesion of fibroblasts to the plate bottom was not observed, and it was confirmed that a cell mass of primary cancer cells having a size of 100 μm or more could be formed. Meanwhile, in the 96-well microplate (Corning Incorporated), which is an ordinary adhesive plane culture plate, or NanoCulture Plate having an uneven scaffolding structure for cell mass formation on a low-adhesive plate, cell mass formation was observed while adhesion of fibroblasts to the plate bottom was also observed. The above results indicate that by performing culture using a low-adhesive culture plate and a medium containing a sol of an extracellular matrix, it is possible to allow a cell mass of primary cancer cells having a sufficient size to form without expansion or proliferation of cells such as fibroblasts other than cancer cells even in suspension culture.

Figures 2, 10:
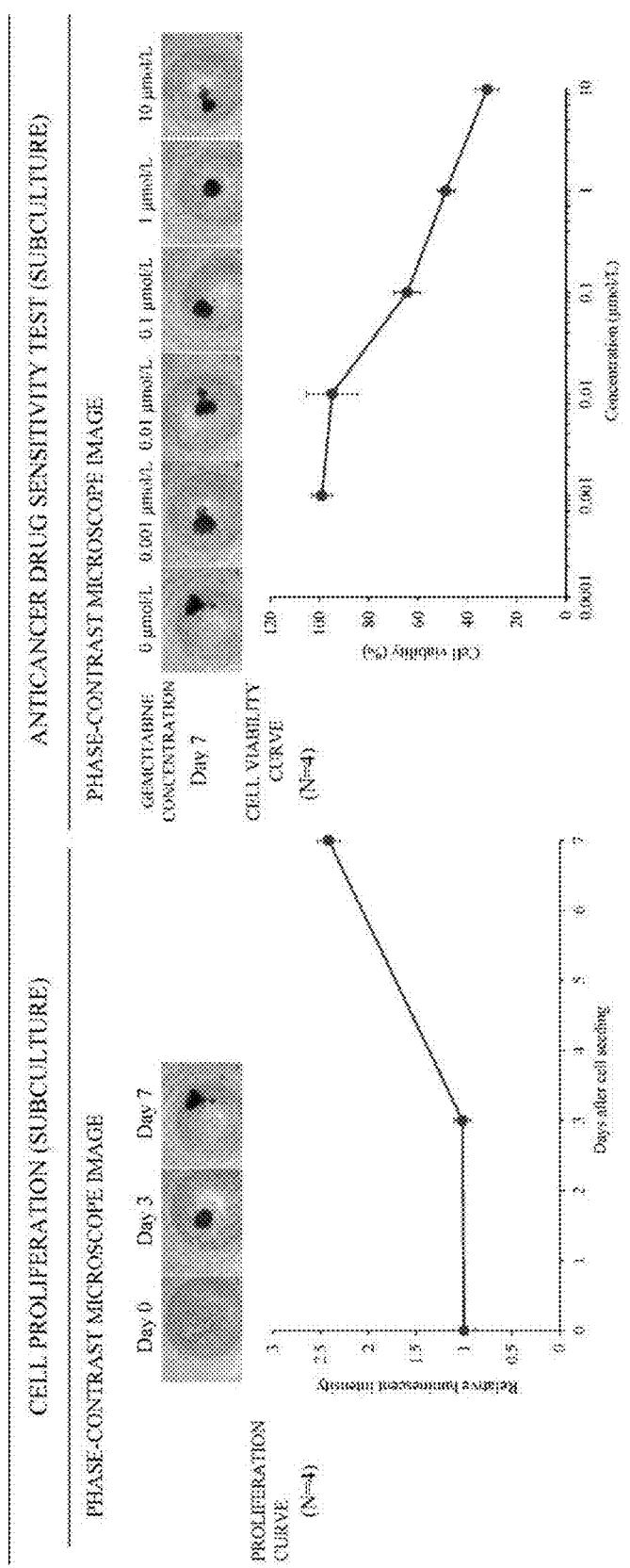

Example 3: Examination of Concentration of Extracellular Matrix to be Added to Medium Primary cancer cells were prepared using pancreatic cancer (1) PDX tumor (procured from National Institutes of Biomedical Innovation, Health and Nutrition) in accordance with Example 1. The necessary amount of cells counted after dispersion treatment were collected in a 15-mL tube, and the supernatant was removed by centrifugation at 300×g for 5 min. Thereafter, a medium prepared by adding Corning Matrigel GFR (Corning Incorporated) to StemPro hESC SFM (Thermo Fisher Scientific K.K.) to yield a final concentration of 0%, 0.5%, 1%, 2%, 5%, 10%, 20%, or 50% v/v was used for preparing cell suspension so that the cell count was $5 \times 10^4$ cells/mL. The cell suspension in an amount of 200 μL was seeded on PrimeSurface (Sumitomo Bakelite Co., Ltd.), and static culture was initiated in a $CO_2$ incubator set to 37° C. and 5% $CO_2$. The seeded cell count was $1 \times 10^4$ cells/200 μL/well, and the day of seeding was determined to be Day 0. No medium exchange was performed, and the enablement of a half of medium exchange was evaluated on Day 14. FIG. 2 shows the results. Cell morphology was confirmed by a phase-contrast microscope. Formation of a cell mass of primary cancer cells having a sufficient size even in suspension was observed without expansion or proliferation of cells other than cancer cells such as fibroblasts at a Corning Matrigel GFR concentration of from 0.5% v/v to 5% v/v. In a case in which when half of the medium in each well was suctioned by pipetting, the medium was not sufficiently in a sol state, and thus, cells or cell mass was suctioned together, it was decided not to perform a half of medium exchange. It was possible to perform a half of medium exchange at 2% v/v or less. It was found that the cell mass could be easily handled and used in various tests.

Example 4: Examination of Type of Extracellular Matrix to be Added to Medium

Figure 4:
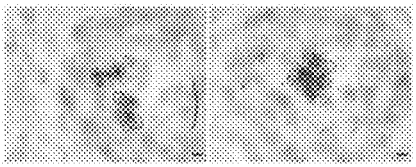
Figure 4:
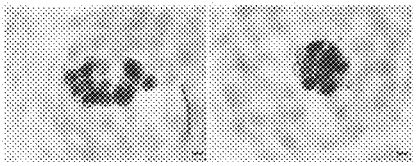
Figure 4:
Figure 4:

Primary cancer cells were prepared using PDX tumor of pancreatic cancer (1) (procured from National Institutes of Biomedical Innovation, Health and Nutrition) in accordance with Example 1. The necessary amount of cells counted after dispersion treatment were collected in a 15-mL tube, and the supernatant was removed by centrifugation at 300×g for 5 min. Thereafter, a medium prepared by adding Corning Matrigel (Corning Incorporated), Cultrex BME (Trevigen, Inc.), Cultrex RGF BME (Trevigen, Inc.), or Cellmatrix Type I-A (Nitta Gelatin Inc.) to StemPro hESC SFM (Thermo Fisher Scientific K.K.) to yield a final concentration of 0%, 0.5%, 1%, 2%, 5%, 10%, or 20% v/v was used for preparing cell suspension so that the cell count was $5 \times 10^4$ cells/mL. The cell suspension in an amount of 200 μL was seeded on PrimeSurface (Sumitomo Bakelite Co., Ltd.), and static culture was initiated in a $CO_2$ incubator set to 37° C. and 5% $CO_2$. The seeded cell count was $1 \times 10^4$ cells/200 μL/well, and the day of screening was determined to be Day 0. No medium exchange was performed, and the enablement of a half of medium exchange was evaluated on Day 14. FIGS. 3-1 to 3-4 show the results. Cell morphology was confirmed visually or by a phase-contrast microscope. Formation of a cell mass of primary cancer cells having a sufficient size even in suspension was observed without expansion or proliferation of cells other than cancer cells such as fibroblasts at a concentration of an extracellular matrix of any of Corning Matrigel, Cultrex BME, Cultrex RGF BME, or Cellmatrix Type I-A from 0.5% v/v to 5% v/v. In a case in which when half of the medium in each well was suctioned by pipetting, the medium was not sufficiently in a sol state, and thus, cells or cell mass was suctioned together, it was decided not to perform a half of medium exchange. A half of medium exchange depended on the type of the extracellular matrix, and it was found possible to perform a half of medium exchange at from 2% to 5% v/v.

Example 5: Examination of Type of Minimal Essential Medium

Primary cancer cells were prepared using PDX tumor of pancreatic cancer (1) (procured from National Institutes of Biomedical Innovation, Health and Nutrition) in accordance with Example 1. After dispersion treatment, the necessary amount of cells counted were collected in a 15-mL tube, and the supernatant was removed by centrifugation at 300×g for 5 min Thereafter, a cell suspension was prepared so that the cell count was $5 \times 10^4$ cells/mL using a medium prepared by adding Corning Matrigel GFR (Corning Incorporated) to StemPro hESC SFM (Thermo Fisher Scientific K.K.) or StemFit AK02N (Takara Bio Inc.) serving as a minimal essential medium to yield a final concentration of 2% v/v. The cell suspension in an amount of 200 μL was seeded on PrimeSurface (Sumitomo Bakelite Co., Ltd.), and static culture was initiated in a $CO_2$ incubator set to 37° C. and 5% $CO_2$. The seeded cell count was $1 \times 10^4$ cells/200 μL/well, and the day of seeding was determined to be Day 0. A half of medium exchange was performed as appropriate. FIG. 4 shows the results. Cell morphology was confirmed by a phase-contrast microscope. Formation of a cell mass of primary cancer cells having a sufficient size even in suspension was observed in the minimal essential medium of either StemPro hESC SFM or StemFit AK02N without expansion or proliferation of cells other than cancer cells such as fibroblasts.

Example 6: Examination of Type of PDX Tumor

Primary cancer cells were prepared using various PDX tumors (procured from National Institutes of Biomedical Innovation, Health and Nutrition) in accordance with Example 1. As various PDX tumors, pancreatic cancer (1), pancreatic cancer (2), lung squamous cell carcinoma (1), lung squamous cell carcinoma (2), lung squamous cell carcinoma (3), gastric cancer (1), and large bowel cancer (1) were used. After dispersion treatment, the necessary amount of cells counted were collected in a 15-mL tube, and the supernatant was removed by centrifugation at 300×g for 5 min. Thereafter, a cell suspension was prepared so that the cell count was $5 \times 10^4$ cells/mL using a medium prepared by adding Corning Matrigel GFR (Corning Incorporated) to StemPro hESC SFM (Thermo Fisher Scientific K.K.) to yield a final concentration of 2% v/v. The cell suspension in an amount of 200 µL was seeded on PrimeSurface (Sumitomo Bakelite Co., Ltd.), and static culture was initiated in a $CO_2$ incubator set to 37° C. and 5% $CO_2$. The seeded cell count was $1 \times 10^4$ cells/200 µL/well, and the day of seeding was determined to be Day 0. A half of medium exchange was performed as appropriate. FIG. 5 shows the results. Cell morphology was confirmed by a phase-contrast microscope. Formation of a cell mass of primary cancer cells having a sufficient size even in suspension was observed regardless of cancer species or type of patient-derived PDX tumor without expansion or proliferation of cells other than cancer cells such as fibroblasts.

Example 7: Histopathological Analysis

Figure 6:
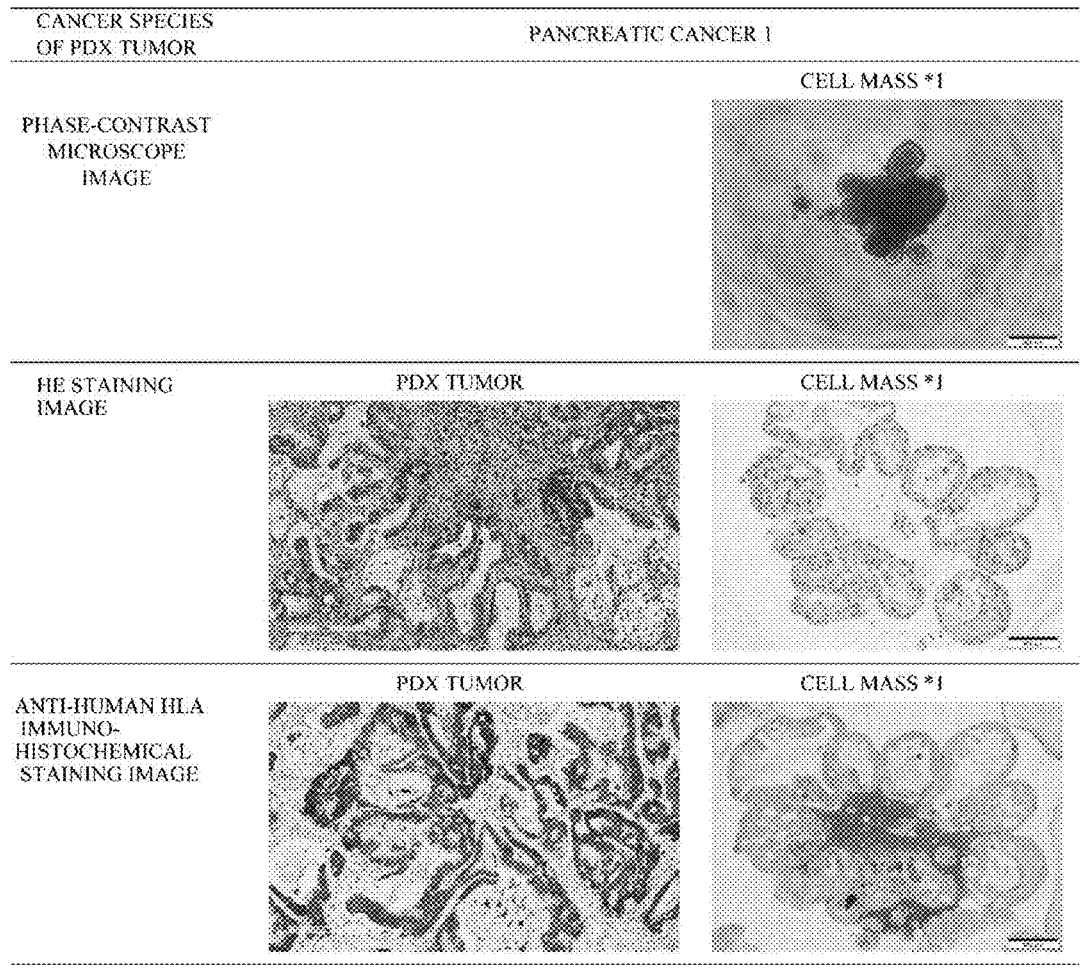
FIG. 6 shows the results of culture in Example 7 (image): *1: a culture medium prepared by adding Corning Matrigel GFR to StemPro hESC SFM to yield a final concentration of 2% v/v was used; PrimeSurface was used as a culture plate; a cell mass of Day 14 was used.

Primary cancer cells were prepared using PDX tumor of pancreatic cancer (1) (procured from National Institutes of Biomedical Innovation, Health and Nutrition) in accordance with Example 1. After dispersion treatment, the necessary amount of cells counted were collected in a 15-mL tube, and the supernatant was removed by centrifugation at 300×g for 5 min Thereafter, a cell suspension was prepared so that the cell count was $5 \times 10^4$ cells/mL using a medium prepared by adding Corning Matrigel GFR (Corning Incorporated) to StemPro hESC SFM (Thermo Fisher Scientific K.K.) to yield a final concentration of 2% v/v. The cell suspension in an amount of 200 µL was seeded on PrimeSurface (Sumitomo Bakelite Co., Ltd.), and static culture was initiated in a $CO_2$ incubator set to 37° C. and 5% $CO_2$. The seeded cell count was $1 \times 10^4$ cells/200 µL/well, and the day of seeding was determined to be Day 0. A half of medium exchange was performed as appropriate. Cell mass was collected in a 1.5-mL tube on Day 14, solidified using iPGell (GENOSTAFF CO., LTD.) to form jelly, and fixed with a 10% neutral buffered formalin solution overnight. In accordance with an ordinary method, a paraffin-embedded specimen was prepared using the formalin-fixed cell mass, and HE staining and anti-human HLA immunohistochemical staining were performed. As a control for comparison, a formalin-fixed paraffin-embedded specimen of a PDX tumor of pancreatic cancer (1) was prepared, and HE staining and anti-human HLA immunohistochemical staining were performed in the same manner FIG. 6 shows the results. The staining results confirmed that a cell mass formed from the PDX tumor of pancreatic cancer (1) was composed of human cancer cells. It was also confirmed that the PDX tumor of pancreatic cancer (1) and the cell mass formed therefrom had a similar structure.

Example 8: Examination of Cell Proliferation

Figure 7:
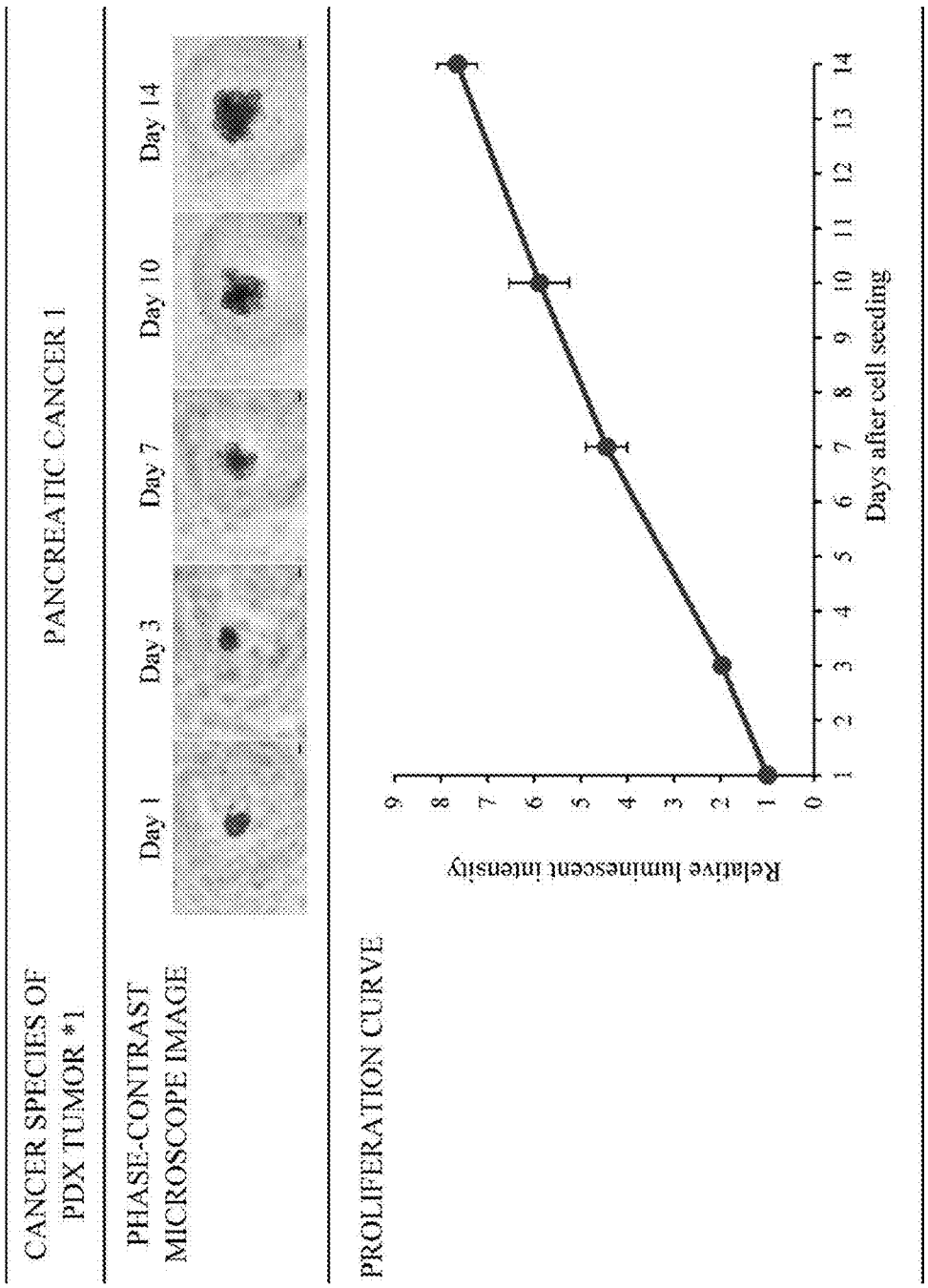
FIG. 7 shows the results of culture in Example 8 (image): *1: a culture medium prepared by adding Corning Matrigel GFR to StemPro hESC SFM to yield a final concentration of 2% v/v was used; PrimeSurface was used as a culture plate.

Primary cancer cells were prepared using PDX tumor of pancreatic cancer (1) (procured from National Institutes of Biomedical Innovation, Health and Nutrition) in accordance with Example 1. After dispersion treatment, the necessary amount of cells counted were collected in a 15-mL tube, and the supernatant was removed by centrifugation at 300×g for 5 min Thereafter, a cell suspension was prepared so that the cell count was $5 \times 10^4$ cells/mL using a medium prepared by adding Corning Matrigel GFR (Corning Incorporated) to StemPro hESC SFM (Thermo Fisher Scientific K.K.) to yield a final concentration of 2% v/v. The cell suspension in an amount of 200 µL was seeded at N=4 (at 4 sites under the same conditions) on PrimeSurface (Sumitomo Bakelite Co., Ltd.), and static culture was initiated in a $CO_2$ incubator set to 37° C. and 5% $CO_2$. The seeded cell count was $1 \times 10^4$ cells/200 µL/well, and the day of seeding was determined to be Day 0. A half of medium exchange was performed on Days 1, 7, 10, and 12. ATP assay was performed using CellTiter-Glo 3D Cell Viability Assay (Promega Corporation) on Days 1, 3, 7, 10, and 14. The proportion of the result of each measurement day with respect to the result of Day 1 was calculated, and a proliferation curve was created. FIG. 7 shows the results. The viable cell count of the cell mass produced from the PDX tumor of pancreatic cancer (1) increased in a time-dependent manner Compared to Day 1, it increased linearly about 4 times on Day 7 and 7 times or more on Day 14. This suggested that the cell mass had high proliferative ability.

Example 9: Anticancer Drug Sensitivity Test

Figure 8:
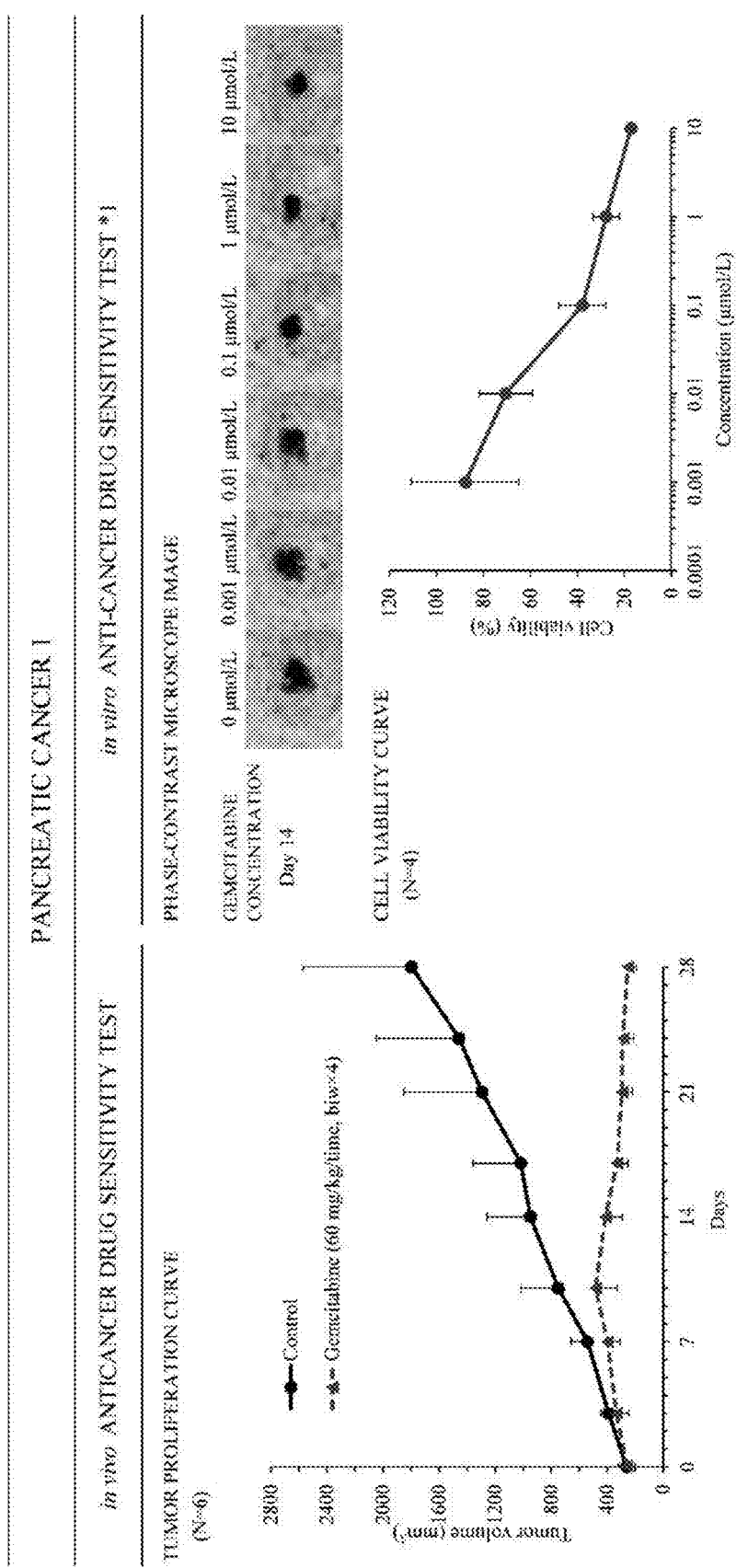
FIG. 8 shows the results of culture in Example 9 (image): *1: a culture medium prepared by adding Corning Matrigel GFR to StemPro hESC SFM to yield a final concentration of 2% v/v was used; PrimeSurface was used as a culture plate. A half of medium exchange was performed with a culture medium supplemented with gemcitabine on Day 7. A half of medium exchange was performed with a culture medium supplemented with gemcitabine which was adjusted to maintain the final concentration on Days 10 and 12. On Day 14, ATP assay was performed, and the proportion based on the result of each gemcitabine concentration group was calculated when the result at a gemcitabine concentration of 0 μmol/L was defined as a cell viability of 100%, thereby creating a cell viability curve.

Primary cancer cells were prepared using pancreatic cancer (1) PDX tumor (procured from National Institutes of Biomedical Innovation, Health and Nutrition) in accordance with Example 1. An in vivo anticancer drug sensitivity test was performed by the following procedures with reference to a known method. A PDX tumor of pancreatic cancer (1), which was subcutaneously grown in an immunodeficient mouse [super SCID mouse (strain name C3H/HeJ/NOs-scid; LPS-nonresponder)], was aseptically extracted in a safety cabinet, and every necrotic area of the tumor was removed with surgical scissors. Subsequently, graft tumor fragments each having a size of about 2 to 3 mm square were prepared and subcutaneously grafted in at least 12 immunodeficient mice. When the average tumor volume reached about 200 $mm^3$, the mice were grouped by tumor volume and assigned to a control group and a gemcitabine administration group (N=6: 6 mice each under the same conditions). Gemcitabine (60 mg/kg/time) was administered at a dosing frequency of twice weekly for 4 weeks. The tumor diameter was measured at a frequency of twice weekly and the tumor volume was calculated, thereby creating a tumor proliferation curve. FIG. 8 (left) shows the results.

An in vitro anticancer drug sensitivity test was performed by the following procedures. After dispersion treatment, the necessary amount of cells counted were collected in a 15-mL tube, and the supernatant was removed by centrifugation at 300×g for 5 min Thereafter, a cell suspension was prepared so that the cell count was $5 \times 10^4$ cells/mL using a medium prepared by adding Corning Matrigel GFR (Corning Incorporated) to StemPro hESC SFM (Thermo Fisher Scientific K.K.) to yield a final concentration of 2% v/v. The cell suspension in an amount of 200 µL was seeded at N=4 (at 4 sites under the same conditions) on PrimeSurface (Sumitomo Bakelite Co., Ltd.), and static culture was initiated in a $CO_2$ incubator set to 37° C. and 5% $CO_2$. The seeded cell count was $1 \times 10^4$ cells/200 µL/well, and the day of seeding was determined to be Day 0. A half of medium exchange was performed on Day 1. On Day 7, a half of medium exchange was performed using a medium to which gemcitabine was added to yield a final gemcitabine concentration of 0, 0.001, 0.01, 0.1, 1, or 10 μmol/L. On Days 10 and 12, a half of medium exchange was performed using a medium which was adjusted to have a stable final gemcitabine concentration. ATP assay was performed using CellTiter-Glo 3D Cell Viability Assay (Promega Corporation) on Day 14. The proportion of the result of each gemcitabine concentration group was calculated when the result at a gemcitabine concentration of 0 μmol/L was defined as a cell viability of 100%, thereby creating a cell viability curve. FIG. 8 (right) shows the results.

Gemcitabine inhibited proliferation of the PDX tumor of pancreatic cancer (1) in both the in vivo and in vitro sensitivity tests.

Example 10: Examination Using Frozen Tumor Tissue

Figure 9:
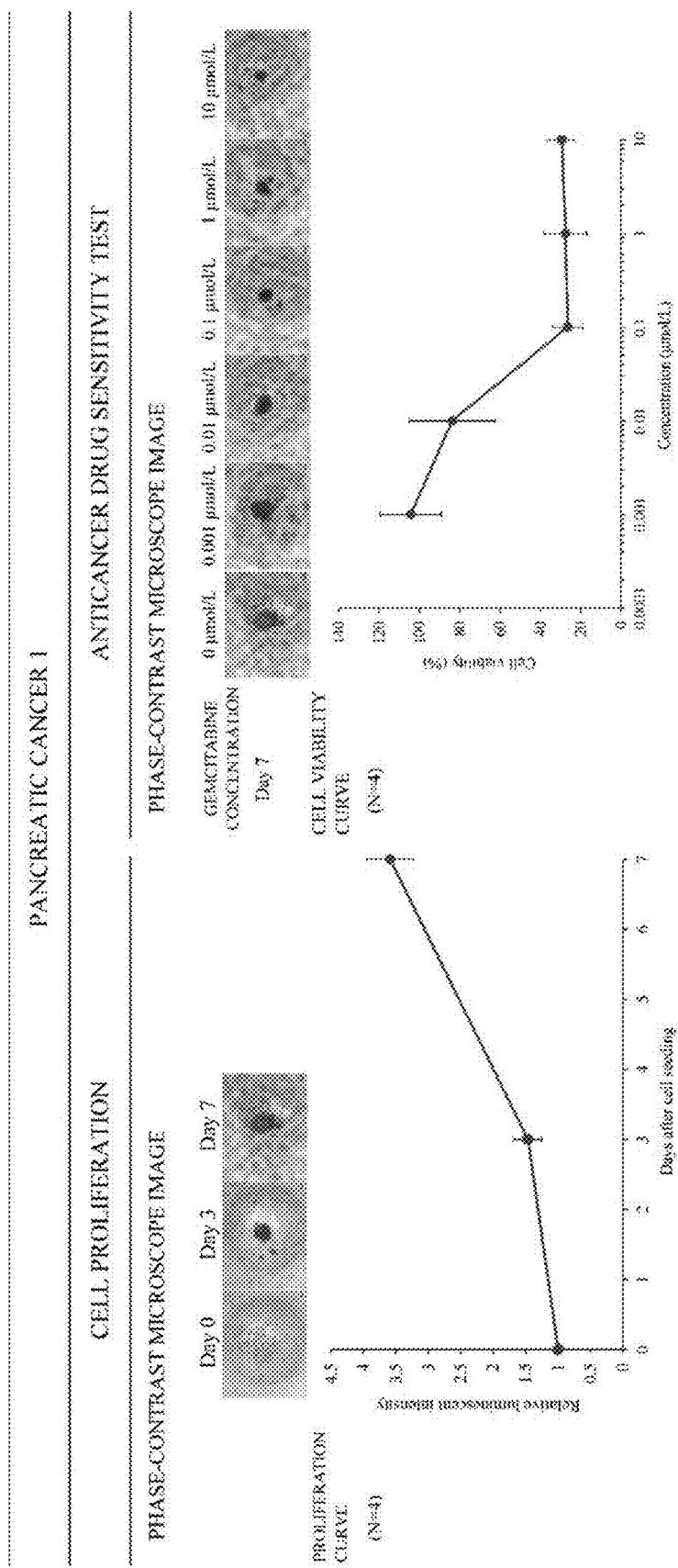
FIG. 9 shows the results of culture in Example 10 (image).

The PDX tumor of pancreatic cancer (1) (procured from National Institutes of Biomedical Innovation, Health and Nutrition) was extracted in accordance with Example 1. The tumor was immersed in CELLBANKER 1 (Takara Bio Inc.) and frozen by a Program Deep Freezer (Nepa Gene Co., Ltd.), thereby preparing a frozen tumor. The frozen tumor was thawed in a warm bath at 37° C. and washed with HBSS (Thermo Fisher Scientific K.K.), and then, primary cancer cells were prepared in accordance with Example 1. After dispersion treatment, the necessary amount of cells counted were collected in a 15-mL tube, and the supernatant was removed by centrifugation at 300×g for 5 min. Thereafter, a cell suspension was prepared so that the cell count was $5 \times 10^4$ cells/mL using a medium prepared by adding Corning Matrigel GFR (Corning Incorporated) to StemPro hESC SFM (Thermo Fisher Scientific K.K.) to yield a final concentration of 2% v/v. The cell suspension in an amount of 200 μL was seeded at N=4 (at 4 sites under the same conditions) on PrimeSurface (Sumitomo Bakelite Co., Ltd.), and static culture was initiated in a $CO_2$ incubator set to 37° C. and 5% $CO_2$. The seeded cell count was $1 \times 10^4$ cells/200 μL/well, and the day of seeding was determined to be Day 0. On Day 3, 50 μL of a medium, to which gemcitabine was added to yield a final gemcitabine concentration of 0, 0.001, 0.01, 0.1, 1, or 10 μmol/L, was added to each well (250 μL/well). ATP assay was performed using CellTiter-Glo 3D Cell Viability Assay (Promega Corporation) on Days 0, 3, and 7. The proportion of the result of each measurement day with respect to the result of Day 0 was calculated, and a proliferation curve was created. The proportion based on the result of each gemcitabine concentration group was calculated when the result at a gemcitabine concentration of 0 μmol/L was defined as a cell viability of 100%, thereby creating a cell viability curve. FIG. 9 shows the results.

The viable cell count of the cell mass produced from the once-frozen PDX tumor of pancreatic cancer (1) increased in a time-dependent manner Compared to Day 0, it increased about 4 times on Day 7. As in Example 9, gemcitabine inhibited proliferation of a cell mass originating from the PDX tumor of pancreatic cancer (1) even with the use of a once-frozen tumor tissue.

Example 11: Examination of Subculture

A fresh tumor-derived cell mass and a frozen tumor-derived cell mass were obtained in accordance with Examples 1 and 10, respectively, using a PDX tumor of pancreatic cancer (1) (procured from National Institutes of Biomedical Innovation, Health and Nutrition). Each cell mass was collected in a 50-mL tube, and the supernatant was removed by centrifugation at 300×g for 5 min. Thereafter, the cell mass was suspended in TrypLE (Thermo Fisher Scientific K.K.) and enzymatically treated in a warm bath at 37° C. The reaction was weakened by adding 10 times the amount of HBSS (Thermo Fisher Scientific K.K.) to the reaction solution. The undispersed residues were removed by passing the mixture through a 100-μm cell strainer. The tube and the cell strainer were washed with an appropriate amount of HBSS, and cells were collected and centrifuged at 300×g for 5 min. The supernatant was removed. Then, HBSS was added to resuspend the resulting cell pellet and centrifuged at 300×g for 5 min. Thereafter, the cell pellet was resuspended with an appropriate amount of HBSS and cell counting was performed. After confirming that the cells were separated into single cells, the cells were used in the following experiment.

The necessary amount of cells were collected in a 15-mL tube, and the supernatant was removed by centrifugation at 300×g for 5 min. Thereafter, a cell suspension was prepared so that the cell count was $5 \times 10^4$ cells/mL (fresh tumor-derived) or $2 \times 10^4$ cells/mL (frozen tumor-derived) using a medium prepared by adding Corning Matrigel GFR (Corning Incorporated) to StemPro hESC SFM (Thermo Fisher Scientific K.K.) to yield a final concentration of 2% v/v. The cell suspension in an amount of 200 μL was seeded at N=4 (at 4 sites under the same conditions) on PrimeSurface (Sumitomo Bakelite Co., Ltd.), and static culture was initiated in a $CO_2$ incubator set to 37° C. and 5% $CO_2$. The seeded cell count was $1 \times 10^4$ cells/200 μL/well (fresh tumor-derived) or $4 \times 10^3$ cells/200 μL/well (frozen tumor-derived), and the day of seeding was determined to be Day 0. On Day 3, 50 μL of a medium, to which gemcitabine was added to yield a final gemcitabine concentration of 0, 0.001, 0.01, 0.1, 1, or 10 μmol/L, was added to each well (250 μL/well). ATP assay was performed using CellTiter-Glo 3D Cell Viability Assay (Promega Corporation) on Days 0, 3, and 7. The ratio of the result of each measurement day with respect to the result of Day 0 was calculated, and a growth curve was created. The proportion based on the result of each gemcitabine concentration group was calculated when the result at a gemcitabine concentration of 0 μmol/L was defined as a cell viability of 100%, thereby creating a cell viability curve. FIGS. 10-1 and 10-2 show the results.

The viable cell count of the cell mass reproduced (also referred to as "subcultured") from the PDX tumor of pancreatic cancer (1) increased in a time-dependent manner regardless whether it was a fresh tumor-derived or frozen tumor-derived cell mass. Compared to Day 0, it increased linearly about 2 times on Day 7. As in Examples 9 and 10, gemcitabine inhibited proliferation of the reproduced cell mass originating from the PDX tumor of pancreatic cancer (1).

INDUSTRIAL APPLICABILITY

According to the invention, it has become possible to provide a method of producing a cell mass by three-dimensional culture of primary cancer cells having proliferative ability and properties of handleability, versatility, and high-throughput performance, in which a human tumor tissue is used as a starting material, proliferation of cells other than cancer cells such as fibroblasts is inhibited, and the cell mass includes primary cancer cells as a main component. Therefore, it becomes possible to easily and inexpensively produce a cell mass from an in vivo tissue, which can contribute to drug screening, drug efficacy evaluation, drug safety evaluation, regenerative medicine, and the like.

What is claimed is:

1. A method of screening for a substance that acts on a cell mass, comprising:
producing a cell mass by three-dimensional culture of primary cancer cells using a tumor tissue, comprising:
culturing cells obtained from the tumor tissue in a medium containing a 5% v/v or less extracellular matrix on a substantially low-adhesive cell culture substrate, and
producing the cell mass of the primary cancer cells;
adding a test substance to the cell mass; and
evaluating an action of the test substance on the cell mass.

2. The method according to claim 1, wherein the tumor tissue is a xenograft tumor.

3. The method according to claim 1, wherein said extracellular matrix is selected from the group consisting of collagen I, collagen IV, fibronectin, laminin, vitronectin, entactin, gelatin, elastin, proteoglycan, glucosaminoglycan, chondroitin sulfate, dermatan sulfate, heparan sulfate, heparin, and keratan sulfate.

4. The method according to claim 1, wherein the cell mass produced by said three-dimensional culture step has an average diameter of 100 μm or more.

5. The method according to claim 1, wherein the substantially low-adhesive cell culture substrate is a culture substrate having a hydrophilic surface or a cell culture substrate having a surface treated with a hydrophilic compound.

6. The method according to claim 1, wherein the medium contains 0.1% v/v to 5% v/v extracellular matrix.

7. The method according to claim 1, wherein said three-dimensional culture step is performed from 2 days to 30 days.

8. The method according to claim 1, wherein said medium is in a sol state.

9. The method according to claim 1, wherein the cell mass produced by said three-dimensional culture step has an average diameter of between 100 μm and 300 μm.

10. The method according to claim 1, wherein the medium contains 0.2% v/v to 5% v/v extracellular matrix.

11. A method of determining effects of a substance on a cell mass, comprising:
producing cell mass by three-dimensional culture of primary cancer cells using a tumor tissue, comprising:
culturing cells obtained from the tumor tissue in a medium containing a 5% v/v or less extracellular matrix on a substantially low-adhesive cell culture substrate, and
producing the cell mass of the primary cancer cells;
adding a test substance to the cell mass; and
evaluating effects of the test substance on the cell mass.

12. The method according to claim 11, wherein the tumor tissue is a xenograft tumor.

13. The method according to claim 11, wherein said extracellular matrix is selected from the group consisting of collagen I, collagen IV, fibronectin, laminin, vitronectin, entactin, gelatin, elastin, proteoglycan, glucosaminoglycan, chondroitin sulfate, dermatan sulfate, heparan sulfate, heparin, and keratan sulfate.

14. The method according to claim 11, wherein the cell mass produced by said three-dimensional culture step has an average diameter of 100 μm or more.

15. The method according to claim 11, wherein the substantially low-adhesive cell culture substrate is a culture substrate having a hydrophilic surface or a cell culture substrate having a surface treated with a hydrophilic compound.

16. The method according to claim 11, wherein the medium contains 0.1% v/v to 5% v/v extracellular matrix.

17. The method according to claim 11, wherein said three-dimensional culture step is performed from 2 days to 30 days.

18. The method according to claim 11, wherein said medium is in a sol state.

19. The method according to claim 11, wherein the cell mass produced by said three-dimensional culture step has an average diameter of between 100 μm and 300 μm.

20. The method according to claim 11, wherein the medium contains 0.2% v/v to 5% v/v extracellular matrix.

* * * * *